US005593385A

United States Patent [19]
Harrison et al.

[11] Patent Number: 5,593,385
[45] Date of Patent: *Jan. 14, 1997

[54] CONTRAST MEDIA DISPENSING APPARATUS

[76] Inventors: Samuel W. Harrison, 4003 Scenic Dr., Shreveport, La. 71119; John Hardin, III, 948 Trabue, Shreveport, La. 71106

[ * ] Notice: The term of this patent shall not extend beyond the expiration date of Pat. No. 5,423,751.

[21] Appl. No.: 409,831

[22] Filed: Mar. 24, 1995

Related U.S. Application Data

[63] Continuation-in-part of Ser. No. 19,048, Feb. 18, 1993, Pat. No. 5,423,751.

[51] Int. Cl.$^6$ .................................................. A61M 3/00
[52] U.S. Cl. ............................................................ 604/83
[58] Field of Search ................................. 604/251–259, 604/246, 248, 80–85, 249, 280, 30–34

[56] References Cited

U.S. PATENT DOCUMENTS

| | | | |
|---|---|---|---|
| 2,866,457 | 12/1958 | Moore | 128/214 |
| 3,001,525 | 9/1961 | Hendricks | 128/214 |
| 3,057,350 | 10/1962 | Cowley | 128/214 |
| 3,533,400 | 10/1970 | Palich | 128/2.05 |
| 3,776,229 | 12/1973 | McPhee | 128/214 C |
| 3,951,145 | 4/1976 | Smith | 128/214 R |
| 4,055,176 | 10/1977 | Lundquist | 128/214 |
| 4,078,563 | 3/1978 | Tuseth | 128/214 |
| 4,175,558 | 11/1979 | Hess, III | 128/214 |
| 4,325,368 | 4/1982 | Kaemmerer | 128/214 R |
| 4,425,123 | 1/1984 | Disalvo | 604/247 |
| 4,428,383 | 1/1984 | Devroom | 128/748 |
| 4,534,757 | 8/1985 | Geller | 604/85 |
| 4,548,598 | 10/1985 | Theeuwes | 604/85 |
| 4,734,091 | 3/1988 | Boyle et al. | 605/54 |
| 4,750,643 | 6/1988 | Wortrich | 222/81 |
| 4,858,619 | 8/1989 | Toth | 128/748 |
| 4,869,457 | 9/1989 | Ewerlof | 251/6 |
| 4,892,524 | 1/1990 | Smith | 604/246 |
| 4,976,685 | 12/1990 | Block, Jr. | 604/52 |
| 5,059,173 | 10/1991 | Sacco | 604/80 |
| 5,074,334 | 12/1991 | Onodera | 137/625.41 |
| 5,078,688 | 1/1992 | Lobodzinski | 604/164 |
| 5,084,031 | 1/1992 | Todd et al. | 604/248 |
| 5,135,026 | 8/1992 | Manska | 137/555 |
| 5,167,643 | 12/1992 | Lynn | 604/263 |
| 5,238,026 | 8/1993 | Goto | 138/30 |
| 5,423,751 | 6/1995 | Harrison et al. | 604/83 |

OTHER PUBLICATIONS

Namic Contrast Controller, Namic U.S.A. Corp. Glens Falls, N.Y.

Merit Contrast Management Product, Merit Medical Systems Inc., South Jordan, Utah. Advertisement in Cath–Lab Digest Jan./Feb. 1995, vol.3 No.1.

*Primary Examiner*—Manuel Mendez
*Attorney, Agent, or Firm*—John M. Harrison

[57] ABSTRACT

A dispensing system and apparatus for introducing contrast media intravascularly during catheterization procedures, which apparatus includes connected segments of tubing that serve as a flow path into the vascular system. A spike is provided at one end of a first segment of the tubing for "spiking" a bottle of contrast media. A stopcock is also provided in the first segment of tubing and a luer lock fitting is attached to the stopcock for connecting a second segment of tubing to the stopcock. A top check valve is provided in the second segment of tubing, which extends from the stopcock. A bottom check valve is provided in the second segment of tubing spaced from the first check valve and a bottom stopcock is also provided in the second segment of tubing below the bottom check valve. A third length of IV tubing projects from the bottom stopcock and receives a second luer lock fitting for securing the bottom end of the third length of IV tubing to a conventional manifold. When the dispensing system is operational, contrast fluid is allowed to flow through the first and second segments of tubing by manipulating the top stopcock, it then flows into the manifold by manipulating the bottom stopcock and is injected intravascularly into the body from the manifold during the catheterization procedure.

11 Claims, 1 Drawing Sheet

CONTRAST MEDIA DISPENSING APPARATUS

CROSS-REFERENCE TO RELATED APPLICATIONS

This application is a Continuation-In-Part of my copending application Ser. No. 08/019,048, Filed Feb. 18, 1993 now U.S. Pat No. 5423751.

BACKGROUND OF THE INVENTION

1. Field of the Invention

Many techniques and various apparatus for administration of various fluids intravenously into the body for a variety of purposes are well known in the art. Solution administration devices are commonly known as intravascular or "IV" systems and generally include a tubular flow line of selected length having a spike at the upper end which may be inserted into an IV solution bag or bottle and a catheter tip at the opposite end for infusing fluid from the bag or bottle into a patient's vein or artery. The flow line or tube also typically includes a flow regulator in the form of a drip chamber and an automated or a thumb-operated device for controlling the rate of fluid flow from the bag or bottle into the flow chamber and to the patient. Variations of this IV system are used during heart catheterization procedures, where a catheter is inserted in a patient's artery or veins, extended into the heart or other area of investigation and a supply of diagnostic radiopaque contrast media is injected from a manifold into the vascular system for angiography in this area. The contrast media is conventionally used for angiography throughout the cardiovascular system, including cerebral and peripheral arteriography, coronary arteriography, ventriculography and the like. Intravascular injection of the radiopaque diagnostic agent contrast media opacifies those vessels in the path of flow of the contrast media, permitting radiographic visualization of the internal structures of the human body. Although the contrast media is particularly well indicated and effective for angiography throughout the cardiovascular system, it is very expensive.

During normal catheterization procedures where contrast media is used, a bottle of contrast media is typically suspended and spiked by one end of a conventional IV apparatus, the opposite end of which is attached to a manifold to facilitate injection of contrast media into the area of investigation at the proper time. Each such procedure requires varying amounts of contrast media and upon completion of each procedure, the IV tubing and unused contrast media, still in the contrast media bottle, are discarded, regardless of the quantity of contrast media remaining in the bottle. This procedure is necessary to avoid the possibility of contamination of the contrast media remaining in the bottle due to pathogens which may reverse-flow by reflux through the IV tubing from the patient into the contrast media. This normal operating technique frequently results in a significant expensive waste for many catheterization procedures, depending upon the quantity of contrast media remaining in the dispensing bottle after the procedure has been completed.

2. Description of the Prior Art

Various types of intravenous systems are well known in the art. Early such apparatus are detailed in U.S. Pat. No. 2,866,457, dated Dec. 30, 1958, to R. C. Moore; U.S. Pat. No. 2,999,499, dated Sep. 12, 1961, to R. H. Willet; U.S. Pat. No. 3,001,525, dated Sep. 26, 1961, to G. E. Hendricks; U.S. Pat. No. 3,057,350, dated Oct. 9, 1962, to C. C. Cowley; U.S. Pat. No. 3,533,400, dated Oct. 13, 1970, to William E. Polich; U.S. Pat. No. 3,776,229, dated Dec. 4, 1973, to Charles J. McPhee; U.S. Pat. No. 3,951,145, dated Apr. 29, 1976, to B. L. Smith; and U.S. Pat. No. 4,055,176, dated Oct. 25, 1977, to I. H. Lundquist. U.S. Pat. No. 4,078,563, dated Mar. 14, 1978, to Robert D. Tuseth, details a "Disc Valve In A Container For Dispensing Liquids". The patent describes an improved disc valve which includes at least two upstanding posts adjacent an outlet passage in the bottom of the container and a floatable disc member with apertures near its periphery, through which the posts extend. The posts are fitted with disc-retaining stops at the upper end and position the disc, and the relationship between the size of the apertures and the thickness of the posts assures that the disc will seat over the outlet passage to prevent the passage of air when all the liquid has been dispensed. U.S. Pat. No. 4,175,558, dated Nov. 27, 1979, to John M. Hess, III, details a "Parenteral Liquid Administering Device" which includes an enlarged chamber for receiving liquid from a source. A bottom flow valve in the chamber controls flow from the chamber, the valve having an air-tight, sealed float system. U.S. Pat. No. 4,325,368, dated Apr. 20, 1982, to E. Kaemmerer, details an infusion device having a dual chamber with two dispensing mechanisms for dispensing two fluids from the chambers. U.S. Pat. No. 4,425,123, dated Jan. 10, 1984, to F. Di Salvo, details a "Parenteral Liquid Application Apparatus". The apparatus includes a liquid flow control device fitted with a membrane which intermittently closes and opens flow communication from beneath the dripping tube. A cannula serves to apply the liquid to the patient, the side of the membrane remote from its control side being connected by a capillary tube to the interior of the dripping tube to equalize the pressure changes occurring on both sides of the membrane as the liquid level and supply vessel decreases. The flow rate is initially adjusted by lowering the level of the liquid stabilization device with respect to the level of the dripping chamber. U.S. Pat. No. 4,428,383, dated Jan. 31, 1984, to W. A. DeVoom, details a "Manifold for Monitoring Hemodynamic Pressure". The manifold assembly includes a base having first, second and third flush valves mounted thereon. A first three-port stopcock is also mounted on the base and has one of its ports in fluid communication with the first flush valve. One of the ports is in fluid flow communication with an arterial catheter and one of the ports is in fluid communication with a pressure monitoring device for determining arterial pressure. The first T-connector is fastened to the second flush valve and a second T-connector is fastened to the third flush valve. A second three-port stopcock is mounted on the base with one of its ports in fluid flow communication with the second flush valve through the first T-connector. One of the ports of the second three-port stopcock is in fluid flow communication with the third flush valve through the second T-connector. U.S. Pat. No. 4,534,757, dated Aug. 13, 1985, to Leo Geller, details a device for releasing an active ingredient into a liquid flow passing through a system for parenterial application of the ingredient. The device includes a receptacle having two half shelves and subdivided by a ribbed aluminum foil into two chambers with an inlet at its upper end and an outlet at the lower end. The chambers have vents at their upper ends and one of the chambers contains two overflows, a first one of which empties into the outlet while the second overflow empties into the other chamber. In the latter chamber, there is present a further overflow which also empties into the outlet, as well as a plate-shaped carrier charged with the active ingredient to be released. The liquid flows from the inlet by means of the first chamber and the second overflow into the other chamber and from there upwardly past a carrier charged with the active ingredient and onward by means of a third overflow and the other chamber into the outlet. U.S. Pat. No. 4,548,598, dated Oct. 22, 1985, to Felix Theeuwes, details a Parenteral Agent Dispensing Equipment which includes a drip chamber and a formulation chamber. The formulation chamber includes a wall surrounding an internal space and has an inlet for admitting a liquid into the formulation chamber and an outlet for letting an agent formulation leave the formulation chamber. The chamber houses an agent delivery system for releasing a beneficial agent into a liquid that enters the chamber. U.S. Pat. No. 4,734,091, dated Mar. 29, 1988, to William J. Boyle, et al, details a "Filtered Manifold Apparatus and Method For Ophthalmic Irrigation". The device is designed to provide ophthalmic irrigation by sterile filtered irrigation fluid into the eye at high flow rates. The apparatus includes a filter capable of removing particles on the order of 0.8 microns and preferably as small as 0.22 microns. A distribution manifold facilitates the flow of fluid from a common reservoir sequentially to multiple recipient sites. U.S. Pat. No. 4,750,643, dated Jun. 14, 1988, to Theodore S. Wortrich, details a "Sterile Fluid Dispensing System and Method". The system is disposable to enable a succession of individuals to be supplied with a sterile medical solution during operative and other procedures. The system uses a number spaced-apart, penetrable, elastomerically sealed funnels branching from an outlet from the solution container or attached drip chamber. A standard sterile administration set having a spike end may be inserted into the seal of a first funnel to provide flow to a first individual. After the first procedure is completed, the conduit to the first funnel is clamped and the sequence is repeated, but with the spiked end of a second administration set inserted for supply to a second individual. The sequence may be repeated for a selected number of branches. U.S. Pat. No. 4,858,619, dated Aug. 22, 1989, to Marie A. Toth, details an "Intracranial Pressure Monitoring System". The device includes a first valve having a first input port and first and second output ports, with the first output port adapted for connection to a drainage collection bag. A tube connects the input port of the first valve to a patient. A second valve has an input port connected to the second output port of the first valve. A dome member has a first opening for connection with an input port of the second valve, a second opening for receiving a pressure transducer and a third opening to permit balancing of the system. Through this configuration, the drainage collection bag is located before the pressure sensor, but at a maximum distance from the patient to reduce the risk of infection and an automatic relief valve may replace the second valve to provide for automatic venting of dangerously high levels of intracranial fluids. U.S. Pat. No. 4,869,457, dated Sep. 26, 1989, to G. Ewerlof, details an "Arrangement For Controlling and Regulating a Liquid Flowing Through a Line". The arrangement includes a valve body provided with a press-on or deforming element movable along the line and designed to cooperate with the line for regulating the flow of the liquid by means of restriction of the liquid to varying degrees. In the line there is fitted a continuous hollow element having a number of openings through which the liquid can flow. The press-on element movable along the hollow element is designed to press the line against the element. In this manner a shifting of the press-on element can be carried out such that an optimal area of the openings can be uncovered for through-flow of the liquid since that part of the hollow element where the area is located is situated on the outlet side with respect to the press-on element. The openings of the hollow element can be uncovered to varying degrees by means of the press-on element arranged in the valve body, the line being pressed against the openings of the hollow element in such a manner that the flow is restricted in varying degrees. An "Intravenous Administration System" is detailed in U.S. Pat. No. 4,892,524, dated Jan. 9, 1990, to Gordon Smith. The apparatus is designed to administer a volumetric flow of parenteral liquids into a patient's system, through which the quantity of liquid flowing into the system may be easily adjusted. The apparatus includes two separate hydrostatic head pressure systems. The first head pressure is applied from a container through a metering device with an adjustable fixed orifice, to a regulator located a fixed distance below the container. The second head is applied from the regulator, which is designed to prevent air flow through it to the patient. U.S. Pat. No. 4,976,685, dated Dec. 11, 1990, to Frank E. Block, Jr., details a "Method of Blood-Gas Interface Control in Surgical Gas Traps". The blood is stored under refrigeration at a temperature of about 4 degrees Centigrade when it is utilized on a relatively rapid basis within a surgical heater. It is transported by tubing through a blood warming apparatus which, while warming the blood, causes an out gas of entrained air. This air is trapped in an air trap receptacle having a drip chamber, within which a gas-blood interface is developed. To assure that the capacity of the trap is not exceeded, an improved technique of gas removal and interface level setting is provided, wherein access is achieved essentially through the entrance region of the gas trap receptacle. U.S. Pat. No. 5,059,173, dated Oct. 22, 1991, to John J. Sacco, details an IV Apparatus. The IV apparatus includes a gravity flow path fluid for administering IV fluids to a patient, in which multiple IV fluids can be delivered at different flow rates to the patient without having to replace the system apparatus. U.S. Pat. No. 5,074,334, dated Dec. 24, 1991, to T. Onodera, details a "Multi-Way Cock". The multi-way cock includes a housing, including multiple branch tubes extending from the periphery thereof, and a plug including a barrel adapted to be rotatably fitted in the cylinder and having a corresponding number of channels formed therein, the channels corresponding to the branch tubes in assembled condition. U.S. Pat. No. 5,078,688, dated Jan. 7, 1992, to Richard Lobodzinski, details a "Paracentesis Catheter System". The system is designed to remove fluid from the patient's abdominal cavity and for administering medication into the abdominal cavity. The catheter system includes a solid stylet, a catheter, a hemostasis valve assembly connected to the catheter and delivery tubing with the needle connecting the catheter assembly to a stopcock. The stopcock has provisions for connection alternately to a syringe or to a vacuum bottle or drainage bag. The hemostasis valve includes an internal gland which is compressed to shutoff fluid flow through the end of the valve assembly after removing the solid styler. This causes fluid to be diverted through the side arm tubing and stopcock to a fluid collection container. U.S. Pat. No. 5,084,031, dated Jan. 28, 1992, to Robert J. Todd, et al, details a "Cardioplegia Three-Way Double Stopcock". The stopcock includes a hollow valve body with three solution infusion ports communicating to the interior thereof in a coplanar arrangement at a first longitudinal point on the valve body. Three cardioplegia pressure monitoring ports also communicate through the valve body to the interior thereof at a second longitudinal position distinct from the first. Mounted in the valve body is a cylindrical valve core selectively rotatable about the longitudinal axis thereof between a first position in which the cardioplegia solution source and the pressure monitor are coupled to the antigrade cannula and a second position in which the cardioplegia solution source and the pressure monitor are coupled to the retrograde catheter formed in the valve core or a set of valving passageways for communicating with selective ones of the infusion ports and a set of valving passageways for communicating with selective ones of the pressure monitoring ports. U.S. Pat. No. 5,135,026, dated Aug. 4, 1992, to Wayne E. Manska, details a "Medical Valve Having Fluid Flow Indicia". The medical valve includes a rotatable member having a fluid flow path formed by a passageway. The flow path indicia on a surface of the rotatable member follows a path along the surface which substantially replicates the fluid flow path of the passage, so as to indicate the orientation of the fluid flow path. U.S. Pat. No. 5,167,643, dated Dec. 1, 1992, to Lawrence A. Lynn, details a "Needle Protection Station". The station is designed for temporarily housing the tip and shaft of a needle or blunt cannula within a protected environment in which an elastomeric core extends into a bore formed in a housing having a tubular shape. An integral shield extends outwardly from the tubular housing between proximal and distal ends and protects the fingers during use. A portion of the housing between the closed end and the shield serves as a handle. Most preferably, the elastomeric core and housing are molded together by insert or core molding. U.S. Pat. No. 5,238,026, dated Aug. 24, 1993, to N. Goto, details a "Liquid Outflow Control Unit". The liquid outflow control unit is used as an instrument for injecting a liquid such as a liquid medicine into a human body. It includes multiple, separate partial members, at least one of which has a groove on a joined face to form a small path through which a liquid may pass. The liquid enters one end of the groove and flows out of an exit and communicates with the other end of the groove. The liquid flowing out of the exit is injected into the human body by means of a connection tube and needle. A "NAMIC Contrast Controller" IV system is marketed by NAMIC U.S.A. Corp. of Glen Falls, N.Y., and includes a spike for spiking a bottle of contrast media, a stopcock and check valve provided in the fluid tubing connected to the spike and a graduated chamber for containing contrast fluid.

It is an object of this invention to provide a contrast media dispensing system or apparatus for dispensing contrast media from a source of supply to a patient, wherein the system allows contrast media unused from a first procedure to be utilized in a second procedure without fear of media contamination during the first procedure.

Another object of this invention is to provide a contrast media dispensing apparatus for safely using substantially all of the contrast media located in a bottle in more than one catheterization procedure, which apparatus includes a spike for spiking a contrast media bottle and a first length of tubing attached to the spike and provided with a top stopcock having a luer lock fitting for attachment to a second length of tubing provided with a pair of spaced check valves and terminating in a bottom stopcock. A third length of tubing extends from the bottom stopcock and is fitted with a luer lock fitting for attachment to a conventional manifold. The contrast media may be selectively drained from the bottle into the manifold during a first catheterization procedure, the entire apparatus below the top stopcock then removed and discarded after the first procedure, a second sterile apparatus attached to the in-place first length of tubing and a second catheterization procedure undertaken without contaminating the contrast media remaining in the bottle.

Yet another object of this invention is to provide a contrast media dispensing apparatus for dispensing contrast media from a supply bottle in multiple sequential catheterization procedures without contaminating the remaining contrast media, which apparatus includes a spike for spiking the contrast media bottle, a vent provided in or near the spike, a first length of IV tubing fitted with a stopcock and a luer lock fitting for attachment to a second length of tubing having a pair of spaced check valves and terminating in a second stopcock. A third length of IV tubing extends from the second stopcock to another luer lock fitting, for attachment to a conventional manifold, wherein the connected second IV tubing, check valves, second stopcock and third IV tubing may be discarded after the first procedure and a second like apparatus attached to the top stopcock, for using substantially all of the contrast media in the bottle without fear of contaminating the contrast media remaining in the bottle during the first or subsequent procedure.

Still another object of this invention is to provide a contrast media dispensing apparatus for dispensing contrast media from a supply bottle in multiple catheterization procedures without contaminating the contrast media during each procedure, which apparatus includes a vented or unvented spike for spiking the rubber plug in the contrast media bottle and a first length of IV tubing fitted with a stopcock having a luer lock fitting for attachment to a second length of IV tubing having a pair of spaced check valves. A third length of IV tubing extends from a second stopcock connected to the second length of IV tubing and the third length of IV tubing terminates in a second luer lock fitting for attachment to a conventional manifold, wherein the second length of IV tubing, check valves, second stopcock and third length of IV tubing may be discarded after the first procedure and a second twin apparatus attached to the top stopcock and the original first length of tubing for using substantially all of the contrast media in the bottle without contaminating the contrast media in the bottle during the first procedure.

SUMMARY OF THE INVENTION

These and other objects of the invention are provided in a contrast media dispensing apparatus for dispensing contrast media-from a supply bottle in multiple catheterization procedures without contaminating the contrast media during each procedure, which apparatus includes a vented or unvented spike for spiking the rubber plug in the contrast media bottle, a first length of IV tubing extending from the spike and terminating at a top, selectively vented, stopcock, a second length of tubing attached to the top stopcock by means of a luer lock and having a top check valve and a bottom check valve spaced from the top check valve, the second length of IV tubing terminating in a bottom stopcock, and a third length of tubing extending from the bottom stopcock and adapted for connecting to a conventional manifold.

BRIEF DESCRIPTION OF THE DRAWING

The invention will be better understood by reference to the accompanying drawing, wherein.

DESCRIPTION OF THE PREFERRED EMBODIMENTS

Figures 1, 2, 3:
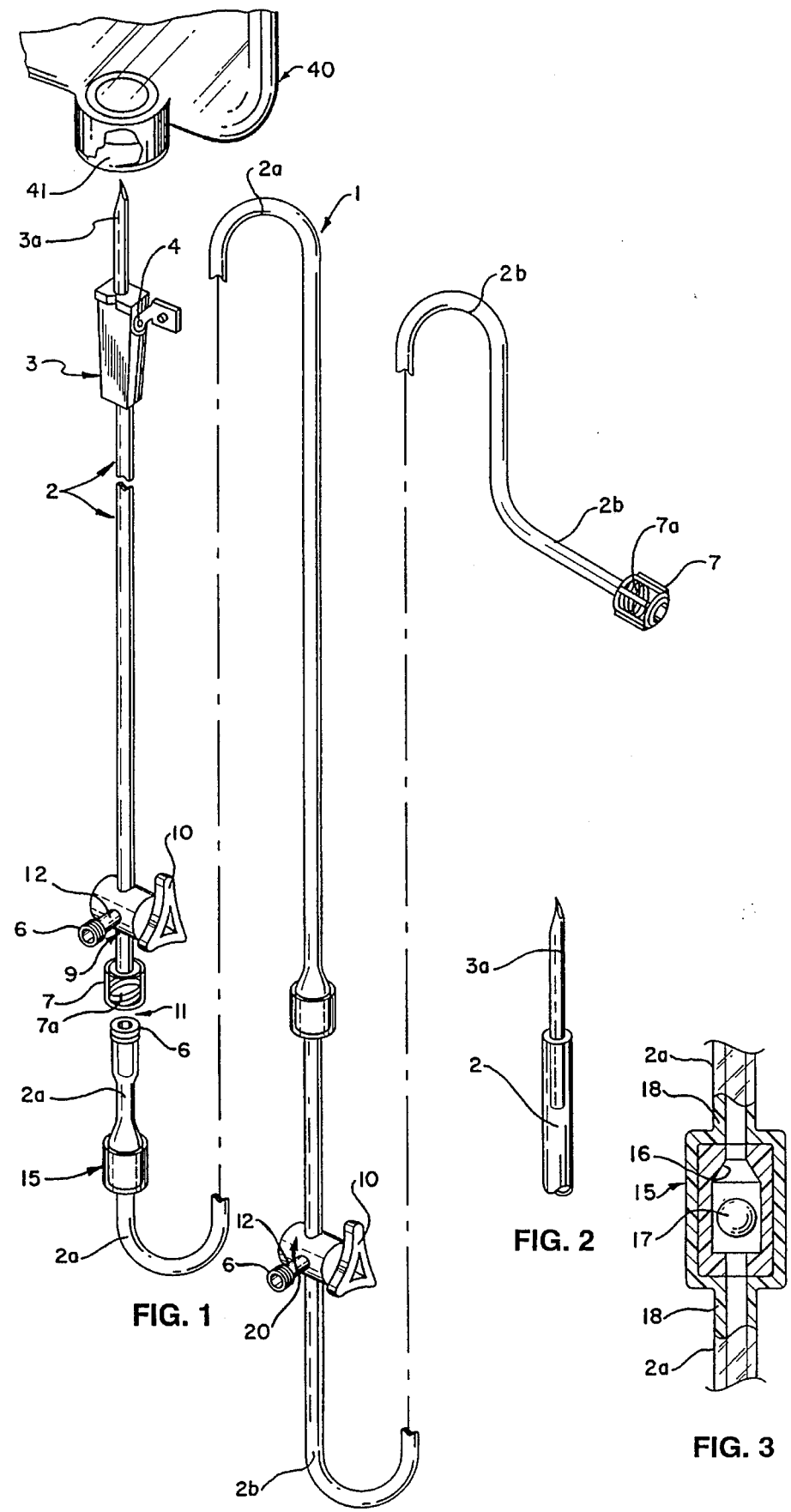
FIG. 1 is a perspective exploded view of a preferred embodiment of the contrast media dispensing apparatus of this invention.
FIG. 2 is an enlarged view of an alternative embodiment of the tubing spike illustrated in FIG. 1.
FIG. 3 is a sectional, enlarged view of typical check valves provided in the contrast media dispensing apparatus illustrated in FIG. 1.

Referring to FIGS. 1–3 of the drawings, the contrast media dispensing apparatus of this invention is generally illustrated by reference numeral 1. The dispensing apparatus 1 includes a first length of tubing 2, having one end fitted with a tubing spike 3, having a spike tip 3a, for extending through or "spiking" a rubber plug 41, located in the mouth of a contrast media bottle 40. The tubing spike 3 thereby accesses a supply of contrast media located in the contrast media bottle 40, for disposition as hereinafter described. A vent 4 is either built into the tubing spike 3 or may be otherwise provided in the first length of tubing 2, for introducing air into the contrast media bottle 40, for purposes which will be hereinafter described. Alternatively, a non-vented tubing spike tip 3a may be provided in the top end of the first length of tubing 2, as illustrated in FIG. 2. The top port of a top stopcock 9, which may be a 3-way stopcock, is attached to the opposite end of the first length of tubing 2 and includes a side port 12, having a luer lock flange 6, and a knob or grip 10, for opening and closing the first length of tubing 2 to facilitate a flow of contrast media from the contrast media bottle 40. A stopcock luer lock 11 facilitates attachment of the top stopcock 9 to one end of a second length of tubing 2a. The stopcock luer lock 1 is conventional in design and includes a luer lock flange 6, secured to one end of the second length of tubing 2a, and a luer lock cap 7 attached to the bottom port of the top stopcock 9. The luer lock flange 6 is designed to engage corresponding cap threads 7a, provided in the companion luer lock cap 7, to removably attach one end of the second length of tubing 2a to the bottom port of the top stopcock 9, for purposes which will also be hereinafter further described. In another preferred embodiment a top check valve 15, a typical design of which is detailed in FIG. 3, is also provided in the second length of tubing 2a below the top stopcock 9, to prevent upward, reverse or reflux flow of contrast media through the second length of tubing 2a and first length of tubing 2, and possible contamination of the contrast media, as further hereinafter described.

The second length of tubing 2a further receives a bottom check valve 22 and the opposite end of the second length of tubing 2a terminates on the top port of a bottom stopcock 20, which is identical in design to the top stopcock 9. A third length of tubing 2b extends from attachment to the bottom port of the bottom stopcock 20 to a luer lock cap 7 for connection to the corresponding luer lock flange (not illustrated) mounted on a conventional manifold (not illustrated), but fully described in my copending U.S. Patent Application, described above. As illustrated in FIG. 3, both the top check valve 15 and bottom check valve 22 may include a pair of top and bottom nipples 18, for extending into the respective connecting second lengths of tubing 2a, as well as a seat 16 and a ball 17, to allow fluid flow from top to bottom by gravity, through the dispensing apparatus 1, but serve to block the reflux of contrast media upwardly from bottom to top. The conventional manifold (not illustrated) is used to inject contrast media intravenously into a patient during the catheterization procedure, according to the knowledge of those skilled in the art and as described in our copending U.S. Patent Application described above.

As illustrated in FIGS. 1–3 of the drawing, under circumstances where it is desirable to use a supply of contrast media stored in a contrast media bottle 40 in a catheterization procedure using the dispensing apparatus 1 illustrated in FIG. 1, the contrast media bottle 40 is initially suspended from a suitable support over a supine patient (not illustrated) in conventional fashion. The top stopcock 9 is then closed to flow of contrast media and the contrast media bottle 40 is "spiked" by forcing the tubing spike 3 through the rubber plug 41, as illustrated. The luer lock cap 7 located on the extending or free end of the third length of tubing 2b is then used to attach the free end of the third length of tubing 2b to the manifold (not illustrated) and the dispensing apparatus 1 is ready for use to selectively dispense contrast media from the contrast media bottle 40, through the connected first length of tubing 2, top stopcock 9, second length of tubing 2a, top check valve 15, bottom check valve 22, bottom stopcock 20 and third length of tubing 2b, into the manifold (not illustrated) and to the patient in conventional fashion. Air may be removed or bled from the first length of tubing 2 and second length of tubing 2a by manipulating the respective grips 10 on the top stopcock 9 and bottom stopcock 20 to the side port 12 position as deemed necessary. Contrast media or fluid is then allowed to flow from the contrast media bottle 40 by again manipulating the respective grips 10 and opening the top stopcock 9 and the bottom stopcock 20 to fluid flow through the first length of tubing 2, second length of tubing 2a and third length of tubing 2b.

Referring again to FIG. 1 of the drawings, if necessary, air can be introduced into the side port 12 of the top stopcock 9 to pressurize the air space in the contrast media bottle 40 and facilitate a more rapid flow of contrast media from the contrast media bottle 90 into the manifold (not illustrated) when the top stopcock 9 and bottom stopcock 20 are opened. Alternatively, opening of the vent 4 in the tubing spike 3 may provide sufficient pressure equalization to effect this rapid flow of contrast media.

While the present invention has been described with the particularity set forth above, it will be understood that modifications will be apparent to those skilled in the art. Accordingly, the invention is limited only by the following claims.

Having described my invention with the particularity set forth above, what is claimed is:

1. A dispensing apparatus for dispensing a fluid from a container to a manifold, comprising a first length of tubing having one end connected in fluid communication to the container; first adjustable valve means connected to the opposite end of said first length of tubing from said one end for controlling the flow of fluid from the container through said first length of tubing; first connecting means provided on said first adjustable valve means; tubing connecting means provided for removably engaging said first connecting means; a second length of tubing having one end connected to said tubing connecting means, whereby said tubing connecting means releasably engages said first connecting means and removably connects said one end of said second length of tubing to said adjustable valve means; a pair of check valves provided in said second length of tubing in spaced relationship with respect to each other; second adjustable valve means attached to the opposite end of said second length of tubing from said one end for further controlling the flow of fluid from the container through said second length of tubing; a third length of tubing having one end attached to said second adjustable valve means; and manifold connecting means provided on the opposite end of said third length of tubing from said one end for removably connecting said third length of tubing to the manifold.

2. The dispensing apparatus of claim 1 comprising a tubing spike carried by said one end of said first length of tubing for connecting said first length of tubing to the container.

3. The dispensing apparatus of claim 2 comprising vent means provided in air communication with said tubing spike for introducing air into said tubing spike and the container and wherein said first adjustable valve means and said second adjustable valve means each comprises a three-way stopcock.

4. The dispensing apparatus of claim 3 comprising vent means provided in air communication with said tubing spike for introducing air into said tubing spike and the container.

5. The dispensing apparatus of claim 2 comprising vent means provided in air communication with said tubing spike for introducing air into said tubing spike and the container.

6. The dispensing apparatus of claim 1 wherein said first adjustable valve means and said second adjustable valve means each comprises a three-way stopcock.

7. In a contrast fluid dispensing system for dispensing a contrast fluid from a container to a point of contrast fluid distribution, the improvement comprising a contrast fluid dispensing apparatus having a first length of tubing connected in fluid communication to the container; a first stopcock terminating said first length of tubing for controlling the flow of fluid from the container through said first length of tubing; a first luer lock fitting provided on said first stopcock; a second luer lock fitting removably engaging said first luer lock fitting on said first stopcock; a second length of tubing having one end connected to said second luer lock fitting; a pair of check valves provided in said second length of tubing in spaced relationship with respect to each other for preventing a reverse flow of contrast fluid from the point of contrast fluid distribution to the container; a second stopcock carried by the opposite end of said second length of tubing from said one end for selectively dispensing fluid from said second length of tubing; a third length of tubing having one end connected to said second stopcock; and a manifold luer lock fitting provided on the opposite end of said third length of tubing from said one end for attachment to the manifold.

8. The contrast fluid dispensing apparatus of claim 7 comprising a tubing spike carried by said first length of tubing for connecting said first length of tubing to the container.

9. The dispensing apparatus of claim 7 comprising vent means provided in air communication with said tubing spike for introducing air into said tubing spike and the container.

10. A contrast fluid dispensing apparatus for dispensing a contrast fluid from a bottle to a manifold, comprising a first length of tubing; a spike provided on one end of said first length of tubing for connecting said first length of tubing to the bottle in fluid communication; a first three-port stopcock provided on the opposite end of said first length of tubing from said one end for controlling a flow of contrast fluid from the bottle through said first length of tubing; a first luer lock attachment provided on said first three-port stopcock; a second length of tubing having one end adapted for removable attachment to said first luer lock attachment; a top check valve provided in said second length of tubing and a bottom check valve provided in said second length of tubing in spaced relationship with respect to said top check valve; a second three-port stopcock provided on the opposite end of said second length of tubing from said one end; a third length of tubing having an end extending from said second three-port stopcock in fluid communication from said second length of tubing to the manifold; and a second luer lock attachment provided on said end extending from said second three-port stopcock for attaching said third length of tubing to the manifold.

11. The contrast fluid dispensing apparatus of claim 10 comprising vent means provided in air communication with said tubing spike for introducing air into said tubing spike and the container.

* * * * *